United States Patent [19]

Bailey

[11] 4,255,418

[45] Mar. 10, 1981

[54] ANTI-ACNE LOTION

[76] Inventor: Florence H. Bailey, 201 W. Illinois Ave., Greensburg, Kans. 67054

[21] Appl. No.: 38,651

[22] Filed: May 14, 1979

[51] Int. Cl.$^3$ ...................... A61K 33/30; A61K 35/78
[52] U.S. Cl. .................................. 424/145; 424/148; 424/168; 424/195; 424/317; 424/346; 424/365
[58] Field of Search ............... 424/145, 148, 365, 195, 424/168

[56] References Cited

U.S. PATENT DOCUMENTS

| | | | |
|---|---|---|---|
| 1,492,823 | 5/1924 | Woll | 424/195 |
| 1,593,959 | 7/1926 | Wade | 424/364 |

OTHER PUBLICATIONS

Handbook of Nonprescription Drugs, 5th ed., 1977, pp. 317-323.
Chemical Abstracts, 68: 107850h (1968).
Sagarin–Cosmetics, Science & Technology (1957).
Gregory–Uses & Applications of Chemicals and Related Materials, vol. II, 1945, p. 341.

*Primary Examiner*—Leonard S. Schenkman
*Attorney, Agent, or Firm*—John H. Widdowson

[57] ABSTRACT

An anti-acne lotion, a method of manufacturing same, and a method of treating skin. The lotion includes zinc oxide, a sodium borate, vinegar, oils, cucumber juice, and hydroxybenzenes.

9 Claims, No Drawings

ANTI-ACNE LOTION

BACKGROUND OF THE INVENTION

1. Field of the Invention

This invention is related to an anti-acne lotion. More specifically, this invention provides an anti-acne lotion, a method of manufacturing same, and a method of treating human skin with the anti-acne lotion.

2. Description of the Prior Art

The following United Statespatents are related to the field of anti-acne lotion: U.S. Pat. Nos. 4,036,991; 2,898,269; 1,593,959; 1,492,823; 3,164,523, and 3,277,616. None of these patents disclose an anti-acne lotion that provide the same benefits as my novel anti-acne lotion.

SUMMARY OF THE INVENTION

It is therefore an object of this invention to provide an anti-acne lotion that cuts and removes sebum, a method of manufacturing the lotion, and a method of treating human skin with the lotion.

It is another object of this invention to provide an anti-acne lotion having a mild antiseptic and drying quality.

It is yet another object of this invention to provide an anti-acne lotion having an emollient which keeps the skin pliable so sebum is not trapped below the skin surface.

It is still yet another object of this invention to provide an anti-acne lotion including healing properties which promote closing of open pores to seal out foreign substances which cause infection.

Other objects of this invention will appear from the following detailed description.

Broadly, this invention provides an anti-acne lotion comprising between about 0.34% by weight and 1.02% by weight of zinc oxide; between about 0.04% by weight and 0.12% by weight of a first compound $Na_2B_4O_7 \cdot n\ H_2O$ wherein n is selected from the group consisting of 0, 5 and 10; between about 1.08% by weight and 3.23% by weight of vinegar; between about 0.68% by weight and 2.03% by weight of castor oil; between about 2.15% by weight and 6.44% by weight of an oil selected from the group consisting of paraffin oil, mineral oil, almond oil, and mixtures thereof; between about 86% by weight and 97% by weight of cucumber juice; and between about 0.68% by weight and 2.03% by weight of a second compound selected from the group consisting of hydroxybenzenes, dihydroxybenzenes, pyrogallol, phloroglucinol, methylpyrogallol, tetrahydroxybenzene, pentahydroxybenzene, hexahydroxybenzene, and mixtures thereof.

The method of beneficially treating human skin comprises applying the anti-acne lotion to the skin. The method of manufacturing the anti-acne lotion includes grinding cucumbers to extract cucumber juice; heating to 212° F. and cooling down to about 114° F.; mixing a predetermined amount of the compounds comprising the anti-acne lotion, excepting one of the oils and castor oil, with each other; mixing a predetermined amount of one of the oils and castor oil with each other; and heating both the oil mixture and the anti-acne lotion compounds (excepting the oil and castor oil) mixture to a temperature to between about 90° F. and 140° F. and combining both heated mixtures while continually stirring same.

DETAILED DESCRIPTION OF THE INVENTION

My novel anti-acne lotion comprises between about 0.34% by weight and 1.02% by weight of zinc oxide; between about 0.04% by weight and 0.12% by weight of a first compound $Na_2B_4O_7 \cdot n\ H_2O$ wherein n is selected from the group consisting of 0, 5 and 10; between about 1.08% by weight and 3.23% by weight of vinegar; between about 0.68% by weight and 2.03% by weight of castor oil; betwe en about 2.15% by weight and 6.44% by weight of an oil selected from the group consisting of paraffin oil, almond oil, mineral oil, and mixtures thereof; between about 86% by weight and 97% by weight of cucumber juice; and between about 0.68% by weight and 2.03% by weight of a second compound selected from the group consisting of hydroxybenzenes, dihydroxybenzenes, pyrogallol, phloroglucinol, methylpyrogallol, tetrahydoxybenzene, pentahydroxybenzene, hexahydroxybenzene, and mixtures thereof. The hydroxybenzenes is a compound selected from the group consisting of phenol, toluylhydroxide, dimethylhydroxybenzene, trimethylhydroxybenzene, durenol (1,2,4,5-tetramethyl-3-hydroxybenzene), carvacrol, pentamethylphenol, and mixtures thereof. Preferably, the hydroxybenzene is phenol. Also preferably, the first compound is $Na_2B_4O_7 \cdot 10\ H_2O$. The dihydroxybenzenes is any compound selected from the group consisting of quinol, thymoquinol, mesorcinol, dihydroxyxylol, orcinol, and mixtures thereof. In a preferred embodiment of my invention, my lotion comprises 0.68% by weight of zinc oxide; 0.08% by weight of $Na_2B_4O_7 \cdot 10\ H_2O$; 2.15% by weight of vinegar; 1.35% by weight of castor oil; 4.29% by weight of medium weight mineral oil; about 90.1% by weight of cucumber juice; and 1.35% by weight of pheno l. The method of beneficially treating humam skin comprises applying to the skin my anti-acne lotion.

My method of manufacturing my anti-acne lotion comprises grinding a plurality of cucumbers in a grinding zone, at ambient conditions, in order to extract from the cucumbers a predetermined amount of cucumber juice (from 86% by weight to 97% by weight). The cucumber juice is subsequently strained or filtered at least once (preferably three times) through a mesh means (e.g. a fine cloth mesh), and then heated to 212° F. Thereafter, the filtered cucumber juice is cooled to between about 90° F. and 140° F. In a preferred embodiment of the invention, the cucumber juice is cooled to about 114° F. Aft the cucumber juice has been prepared (on or before, the order is not of importance), a predetermined amount of each of the following compounds is mixed with each other at ambient conditions: between about 0.34% by weight and 1.02% by weight of zinc oxide; between about 0.04% by weight and 0.12% by weight of a first compound $Na_2B_4O_7 \cdot n\ H_2O$ wherein n is selected from the group consisting of 0.5 and 10; between about 1.08% by weight and 3.23% by weight of vinegar; between about 0.68% by weight and 2.03% by weight of a second compound selected from the group consisting of hydroxybenzenes, dihydroxybenzenes, pyrogallol, phloroglucinol, methylpyrogallol, tetrahydroxybenzene, pentahydroxybenzene, hexahydroxybenzene, and mixtures thereof. For heat conservation purposes, this prepared mixture is heated to between about 90° F. and 140° F.; most preferably, to 114° F.; prior to admixing the cooled 114° F. cucumber juice therewith. If the cucumber juice is added prior to heating, the ambient condition compounds would cause the temperature of the cucumber juice to drop to an undesirable temperature (i.e. below between about 90° F. and 140° F.) and the whole combination of substances would have to be heated to between about 90° F. and 114° F., instead of only the ambient condition substances. After the ambient conditions substances have been heated to between about 90° F. and 140° F. and admixed with the (between 86% by weight and 97% by weight) cucumber juice possessing the same temperature (or prior to preparing and heating these two substances; again, order is of no importance), between about 2.15% by weight and 6.44% by weight of an oil selected from the group consisting of paraffin oil, almond oil, mineral oil, and mixtures thereof, is mixed with between about 0.68% by weight and 2.03% by weight of castor oil, and subsequently heated to between about 90° F. and 140° F. In a preferred embodiment of the invention, the oil mixture is heated to about 114° F. Subsequently, the heated oil mixture and the heated cucumber juice - ambient condition substances are admixed at the selected temperature between 90° F. and 114° F. while continually stirring for a predetermined time which is at least one minute and depends on the quantity of each substance utilized in the preparation. For example, I have found that continual stirring must be for 8-10 minutes if the following combination of substances are used in my anti-acne lotion: 5 oz. of zinc oxide, ½ oz. of $Na_2B_4O_7.10\ H_2O$, 16 oz. of vinegar, 10 oz. of castor oil (odorless), 32 oz. of medium weight mineral oil, 10 oz. of phenol, 675 oz. of cucumber juice. I have discovered that for optimum results, all temperatures must be maintained constant at 114° F., especially while combining the 114° F. oil mixture with the 114° F. cucumber juice - ambient condition substances; and I have discovered that while combining, stirring must be continual for optimal results. The oil is preferably combined with the liquid little by little.

The invention will now be described in a number of examples, but it should be understood that these are given by way of illustration and not of limitation and that many changes in the details may be made without departing from the spirit of the invention.

EXAMPLE I

Assuming the previously described manufacturing procedure is followed in preparing my anti-acne lotion comprising: 0.68% by weight zinc oxide, 0.08% by weight $Na_2B_4O_7.10\ H_2O$; 2.15% by weight of vinegar; 1.35% by weight castor oil; 4.29% by weight of medium weight mineral oil; 90.1% by weight cucumber juice; and 1.35% by weight of phenol. Apply this lotion at least once daily to human skin and find skin condition improved and acne under control.

EXAMPLE II

Repeat Example I but vary the percentage (%) by weight in 0.20% by-weight increments of each of the following compounds in the following % by weight ranges and find similar results: zinc oxide 0.34%-1.02% by weight; vinegar 1.08%-3.23% by weight; castor oil 0.68%-2.03% by weight; mineral oil 2.15%-6.44% by weight; and phenol 0.68%-2.03% by weight.

EXAMPLE III

Repeat Example II but vary the percentage (%) by weight in 0.02%—by-weight increments of $Na_2B_4O_7.10$ $H_2O$ in the range of 0.04%-0.12% by weight and vary n to 0 and 5 and find similar results.

EXAMPLE IV

Repeat Example III but vary the percentage (%) by weight in 2%—by-weight increments of cucumber juice in the range of 86%-97% by weight and find similar results.

EXAMPLE V

Repeat Example IV but vary the mineral oil to paraffin oil and/or almond oil and find similar results.

EXAMPLE VI

Repeat Example V but replace the phenol with another compound selected from the group consisting of hydroxybenzenes (toluylhydroxide, dimethylhydroxybenzene, trimethylhydroxybenzene, durenol, carvacrol, pentamethylphenol), dihydroxybenzenes, (quinol, thymoquinol, mesorcinol, dihydroxyxylol, orcinol), pyrogallol, phloroglucinol, methylpyrogallol, tetrahydroxybenzene, pentahydroxybenzene, hexahydroxybenzene, and mixtures thereof.

I have found that if desired essence of oil perfume can be added to any of the new compositions of matter of my invention set forth hereinbefore.

It is understood that the foregoing detailed is given merely by way of illustration and that many variations may be made therein without departing from the spirit of my invention.

I claim:

1. A method of manufacturing an anti-acne lotion comprising:
   (a) grinding a plurality of cucumbers in a grinding zone to extract from said cucumbers between about 86% wt and 97% wt of cucumber juice;
   (b) heating said cucumber juice of step (a) to 212° F.;
   (c) cooling subsequently said heated juice of step (b) to between about 90° F. and 140° F.;
   (d) mixing each of the following compounds with each other: between about 0.34% wt and 1.02% wt of zinc oxide; between about 0.04% wt and 0.12% wt of a $Na_2B_4O_7 \cdot nH_2O$ wherein n is selected from the group consisting of 0, 5, and 10; between about 1.08% wt and 3.23% wt of vinegar; between about 0.68% wt and 2.03% wt of a compound selected from the group consisting of hydroxybenzenes, dihydroxybenzenes, pyrogallol, phloroglucinol, methylpyrogallol, tetrahydroxybenzene, pentahydroxybenzene, hexahydroxybenzene, and mixtures thereof;
   (e) heating said mixture of step (d) to between about 90° F. and 140° F.;
   (f) admixing the heated mixture of step (e) with the cooled cucumber juice of step (c);
   (g) mixing between about 2.15% wt and 6.44% wt of an oil selected from the group consisting of paraffin oil, almond oil, mineral oil, and mixtures thereof; and between about 0.68% wt and 2.03% wt of castor oil, with each other;
   (h) heating said mixture of step (g) to between about 90° F. and 140° F.; and
   (i) combining said mixture of step (f) with the mixture of step (h), at a temperature of between about 90° F. and 140° F., continually stirring while combining.

2. The method of claim 1 additionally including straining at least once said cucumber juice of step (a) prior to heating same.

3. The method of claim 1 wherein said heating step (e) is at about 114° F., said cooling step (c) is at about 114° F. and said combining step (i) is at about 114° F.

4. An anti-acne lotion prepared by the method of claim 1.

5. An anti-acne lotion prepared by the method of claim 2.

6. An anti-acne lotion prepared by the method of claim 3.

7. A method of treating acne on human skin comprising applying to the human skin an effective amount of the anti-acne lotion of claim 4.

8. A method of treating acne on human skin comprising applying to the human skin an effective amount of the anti-acne lotion of claim 5.

9. A method of treating acne on human skin comprising applying to the human skin an effective amount of the anti-acne lotion of claim 6.

* * * * *